(12) United States Patent
Wiggermann (10) Patent No.: US 11,950,968 B2
(45) Date of Patent: Apr. 9, 2024

(54) SURGICAL AUGMENTED REALITY

(71) Applicant: TRUMPF MEDIZIN SYSTEME GMBH + CO. KG, Saalfeld (DE)

(72) Inventor: Neal Wiggermann, Batesville, IN (US)

(73) Assignee: TRUMPF MEDIZIN SYSTEME GMBH + CO. KG, Saalfeld (DE)

(*) Notice: Subject to any disclaimer, the term of this patent is extended or adjusted under 35 U.S.C. 154(b) by 536 days.

(21) Appl. No.: 17/190,673

(22) Filed: Mar. 3, 2021

(65) Prior Publication Data

US 2021/0282887 A1 Sep. 16, 2021

Related U.S. Application Data

(60) Provisional application No. 62/988,988, filed on Mar. 13, 2020.

(51) Int. Cl.
*A61B 90/00* (2016.01)
*A61B 17/00* (2006.01)
*A61B 34/00* (2016.01)
*A61B 34/20* (2016.01)
*A61B 90/50* (2016.01)

(52) U.S. Cl.
CPC .......... *A61B 90/361* (2016.02); *A61B 34/20* (2016.02); *A61B 34/25* (2016.02); *A61B 90/39* (2016.02); *A61B 90/50* (2016.02); *A61B 2017/00221* (2013.01); *A61B 2034/2048* (2016.02); *A61B 2034/2055* (2016.02); *A61B 2034/252* (2016.02); *A61B 2090/365* (2016.02); *A61B 2090/3983* (2016.02); *A61B 2090/502* (2016.02)

(58) Field of Classification Search
CPC ....... G06T 19/006; A61B 34/20; A61B 34/25; A61B 90/361; A61B 90/39; A61B 90/50; A61B 2017/00221; A61B 2034/2048; A61B 2034/2055; A61B 2034/252; A61B 2090/365; A61B 2090/3983; A61B 2090/502
USPC ....................................................... 345/633
See application file for complete search history.

(56) References Cited

U.S. PATENT DOCUMENTS

| 11,244,508 | B2* | 2/2022 | Kazanzides | ........ G02B 27/0172 |
| 2002/0190923 | A1 | 12/2002 | Ronzani et al. | |
| 2005/0128184 | A1 | 6/2005 | McGreevy | |
| 2006/0142739 | A1 | 6/2006 | Disilestro et al. | |
| 2007/0247316 | A1 | 10/2007 | Wildman et al. | |

(Continued)

FOREIGN PATENT DOCUMENTS

WO 2018203304 A1 11/2018

OTHER PUBLICATIONS

"Novarad's OpenSight Augmented Reality System is the First Solution for Microsoft HoloLens 510(k) Cleared by the FDA for Medical Use", BusinessWire, Novarad, link: https://www.businesswire.com/news/home/20181024005714/en/Novarad%E2%80%99s-OpenSight-Augmented-Reality-System-Solution-Microsoft, Oct. 24, 2018, Retrieved on Dec. 16, 2019, p. 1-3.

*Primary Examiner* — Jacinta M Crawford
(74) *Attorney, Agent, or Firm* — Barnes & Thornburg LLP (57) ABSTRACT

Devices, systems, and methods for augmented reality in surgical environments include an optical lens, which may be wearable by the user, and an augmented reality control system for generating an augmented reality presentation in the optical lens. The augmented reality presentation can depict the surgical area of the patient while artificially omitting one or more obstructions from the user's view point of the surgical area.

15 Claims, 9 Drawing Sheets

(56) References Cited

U.S. PATENT DOCUMENTS

| | | | |
|---|---|---|---|
| 2008/0097176 A1 | 4/2008 | Music et al. | |
| 2009/0112630 A1 | 4/2009 | Collins et al. | |
| 2010/0149213 A1 | 6/2010 | Navab et al. | |
| 2012/0123223 A1 | 5/2012 | Freeman et al. | |
| 2014/0139405 A1 | 5/2014 | Ribble et al. | |
| 2014/0145915 A1 | 5/2014 | Ribble et al. | |
| 2018/0168741 A1* | 6/2018 | Swayze | A61B 90/37 |
| 2019/0110685 A1* | 4/2019 | Pautsch | A61B 34/20 |
| 2019/0192230 A1 | 6/2019 | Siemionow et al. | |
| 2019/0246088 A1 | 8/2019 | Casas | |
| 2019/0254754 A1 | 8/2019 | Johnson et al. | |
| 2019/0328462 A1 | 10/2019 | Liu et al. | |
| 2021/0169578 A1* | 6/2021 | Calloway | A61B 90/50 |

\* cited by examiner

SURGICAL AUGMENTED REALITY

CROSS-REFERENCE

This U.S. Non-provisional patent application claims the benefit of priority of U.S. Provisional Patent Application No. 62/988,988, filed on Mar. 13, 2020, entitled "AUGMENTED REALITY FOR ROBOTIC ASSISTED SURGERY", the contents of which are hereby incorporated by reference in their entirety, including but without limitation, those portions concerning augmented reality and surgical aspects.

BACKGROUND

The present disclosure relates to devices, systems, and methods for augmented reality in medical fields, and more specifically, the present disclosure relates to devices, systems, and methods for augmented reality in medical treatment, such as surgical fields.

Augmented reality systems, including systems providing visual augmentation, can provide robust information for consideration. Augmented visual reality systems can provide information to the user in a manner that is assisted by visualizations not commonly available. For example, overlaying detail onto normal visual fields can enhance the user's active work field providing ease of efforts and/or reducing error rates.

In medical treatment fields, such as surgical fields, augmented reality can provide a particularized visual field for the caregiver. By refining the visual field through augmentation, the caregiver can be better informed regarding the surgical process and/or the patient care and/or treatment regime.

SUMMARY

The present application discloses one or more of the features recited in the appended claims and/or the following features which, alone or in any combination, may comprise patentable subject matter.

According to an aspect of the present disclosure, a surgical augmented reality system, may comprise an optical lens through which a user can directly observe surgical procedures, the optical lens configured for presenting visual information augmenting observation of the user. The surgical augmented reality system may include an augmented reality control system arranged in communication with the optical lens to provide presentation of visual information augmenting observation by the user. The control system may comprise at least one processor, at least one memory storage for storing instructions for execution by the at least one processor, and communication circuitry for communicating signals according to the processor. The augmented reality control system may be configured to receive indication of at least one reference datum and to communicate with the optical lens to provide an augmented reality presentation of a surgical area of the patient artificially omitting one or more obstructions from the user's view point of the surgical area.

In some embodiments, the augmented reality presentation may include display of the augmented reality presentation visually arranged in the optical lens offset from the surgical area of the patient to appear as an offset view screen. The augmented reality presentation may include display of the augmented reality presentation visually arranged in the optical lens for observation by the user to appear stationary with reference to the surgical area under relative movement of the optical lens. The optical lens may be configured as a wearable lens.

In some embodiments, the optical lens may be formed as a set of optical glasses comprising at least one sensor for capturing indication of a position of the at least one reference datum. The at least one reference datum may include one or more reference datum arranged on a ceiling of an operating room of the patient. The at least one reference datum may include one or more reference datum arranged on a surgical patient support table.

In some embodiments, the augmented reality control system may be arranged in communication with a surgeon interface for control of a robotic surgery device. The augmented reality control system may be arranged in communication with a remote network. The remote network may be a hospital network.

In some embodiments, the augmented reality control system may be arranged in communication with one or more local surgical devices. The one or more local surgical devices may include at least one of a local server and local surgical instruments.

In some embodiments, the augmented reality control system may be arranged at least partly on a wearable device comprising the optical lens. The augmented reality control system may be arranged at least partly on a surgical server. In some embodiments, the augmented reality presentation may be arranged by the optical lens to overlay the surgical area of the patient to create impression of direct observation.

According to another aspect of the present disclosure, an augmented reality surgical system, comprising a robotic surgery system comprising at least one robotic surgical appendage; and an optical lens through which a user can directly observe surgical procedures involving the robotic surgical appendage, the optical lens configured for presenting visual information augmenting observation of the user. The surgical augmented reality system may include an augmented reality control system in communication with the optical lens to provide presentation of visual information augmenting observation by the user. The control system may comprise at least one processor, at least one memory storage for storing instructions for execution by the at least one processor, and communication circuitry for communicating signals according to the processor. The augmented reality control system may be configured to receive indication of at least one reference datum and to communicate with the optical lens to provide an augmented reality presentation of a surgical area of the patient artificially omitting one or more obstructions from the user's view point of the surgical area.

In some embodiments, the augmented reality control system may be arranged in communication with the robotic surgery system to receive communication of position of the at least one robotic surgical appendage. The augmented reality presentation may include display of the augmented reality presentation visually arranged in the optical lens offset from the surgical area of the patient to appear as an offset view screen. The augmented reality presentation may include display of the augmented reality presentation visually arranged in the optical lens for observation by the user to appear stationary with reference to the surgical area under relative movement of the optical lens.

In some embodiments, the optical lens may be configured as a wearable lens. The optical lens may be formed as a set of optical glasses comprising at least one sensor for capturing indication of a position of the at least one reference datum. The at least one reference datum may include one or more reference datum arranged on a ceiling of an operating room of the patient. The at least one reference datum may include one or more reference datum arranged on a surgical patient support table.

In some embodiments, the augmented reality control system may be arranged in communication with a surgeon interface of the robotic surgery system. The augmented reality control system may be arranged in communication with a remote network. The remote network may include a hospital network.

In some embodiments, the augmented reality control system may be arranged in communication with one or more local surgical devices. The one or more local surgical devices may include at least one of a local server and local surgical instruments.

In some embodiments, the control system may be arranged at least partly on a wearable device comprising the optical lens. The augmented reality control system may be arranged at least partly on a surgical server.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

For the purposes of promoting an understanding of the principles of the disclosure, reference will now be made to a number of illustrative embodiments illustrated in the drawings and specific language will be used to describe the same.

Patient care procedures, such as surgical procedures performed in an operating room of a hospital, can be performed using a variety of equipment and/or instruments. As care procedures advance, the number and/or complexity of the equipment and/or instruments can increase. The result is that the environment of the procedure can be highly occupied and/or encumbered which can create challenges of access and/or observation of the patient and/or the immediate environment of the care procedure in general.

Figure 1:
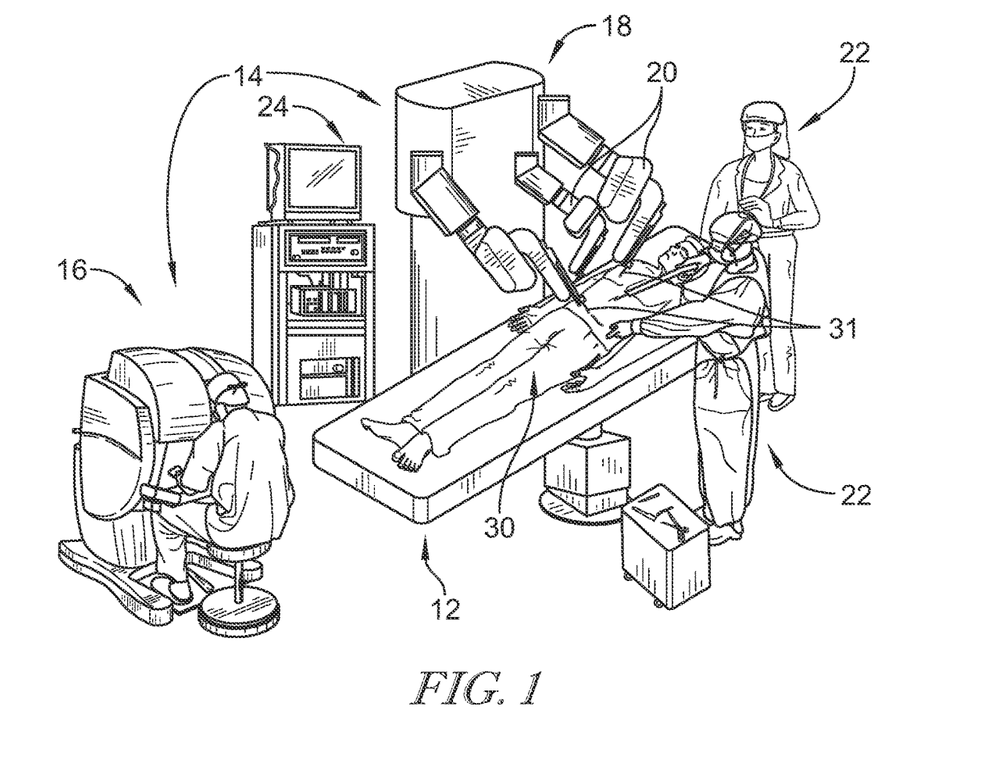
FIG. 1 is a perspective view of a surgical area within a room of a care facility in which a surgical patient is supported by a patient support to receive surgical treatment, including via a robotic surgical system, which can be communicate with an augmented reality system as a part of an augmented reality surgical system to provide an augmented visual field to caregivers.

In the context of robotic procedures, such as robotic-assisted surgical procedures, such encumbrance concerns can be particularly acute. Referring to FIG. 1, a robotic procedure is depicted with a patient supported by a patient support 12 being addressed by a robotic care system 14 embodied as a robotic surgery system. The robotic surgery system 14 is illustratively embodied as a surgeon-directed, computer controlled surgical system for performing surgical procedures.

The robotic surgery system 14 illustratively includes a user interface 16 embodied as a surgeon interface for communicating surgical operations with the surgeon, a robotic personage 18 including at least one robotic appendage 20 for conducting surgical operations according to the direction of the surgeon, and a surgical control system for communicating with the surgeon via the user interface 16 and implementing surgical control of the robotic personage 18 according to the input from the surgeon. The user interface 16 is embodied as a surgical station and may include a graphical display for presenting to the surgeon video and/or other imaging of the patient and/or surgical area of the patient, and controls for user input including surgical controls for manipulation of the robotic personage 18 including the robotic appendages 20. Examples of suitable robotic surgical systems can include for example, Da Vinci robotic surgical systems as marketed by Intuitive Surgical Inc. of Sunnyvale, Calif.

Referring still to FIG. 1, one or more caregivers 22 may assist the procedure. For example, the caregivers 22 may perform auxiliary tasks related to the robotic surgery system 14, such as configuring and/or changing tools connected with the robotic appendages 20 during the procedure, among other things. Moreover, the caregivers 22 may perform surgical tasks such as manually implementing hand tools in conjunction with robotic surgery tasks. The caregivers 22 and/or the surgeon may have access to view a display screen 24 for information regarding the procedure, such as video and/or other imaging of the surgical area of the patient.

Figure 2:
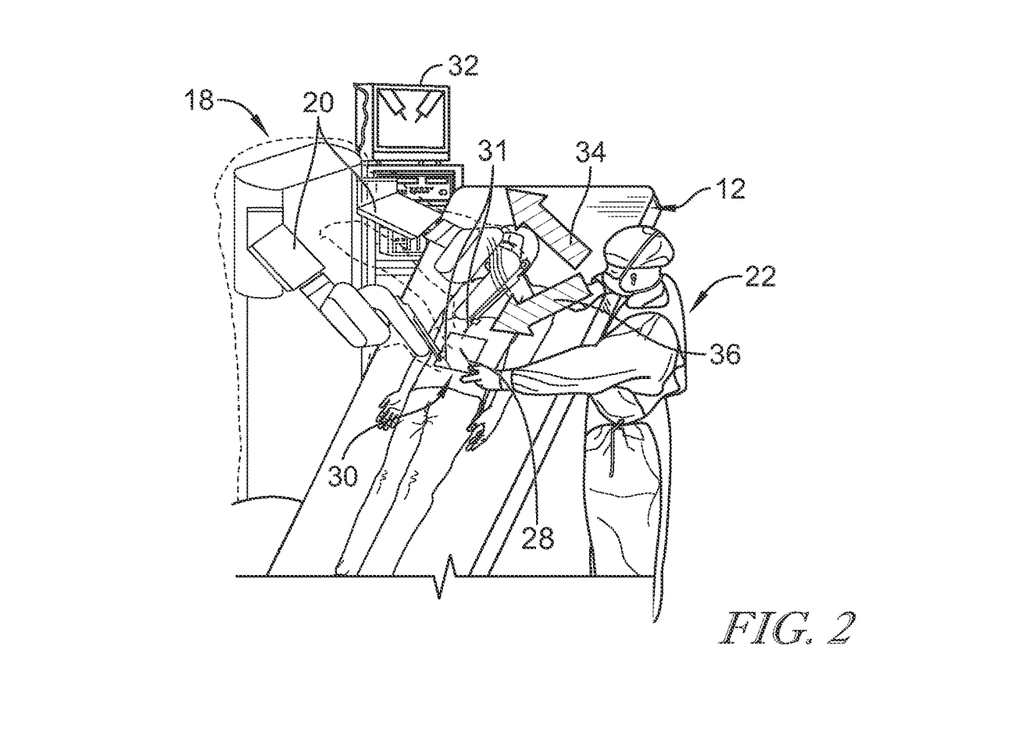
FIG. 2 is perspective view of a robotic surgery system addressing a patient surgical site with a caregiver nearby assisting the procedure, showing that visual access to the surgical site is considerably encumbered by robotic arms, instruments, and other surgical items many of which are draped with protective sheathing, and showing that a caregiver can be required to move considerably to view physical monitors away from the patient surgical site.

Referring now to FIG. 2, an example of the arrangement of items in the environment of the procedure is shown. The patient occupying the patient support 12 is being addressed by two robotic appendages (arms) 20 of the robotic personage 18, and the caregiver 22 is addressing the patient with another manual instrument 28 at a surgical site 30. In the illustrative embodiment, additional instruments 31, which may include instruments held in place by an adjustable stationary hold device, address the patient at the surgical site 30. The number and/or position of the various instruments and equipment near the surgical site 30 can encumber the caregiver's view of the surgical site 30. Notably, each of the robotic appendages 20 and the additional instruments 31 are each draped by protective sheathing (shown in broken line in FIG. 2), illustratively embodied as transparent plastic sheaths to protect the items from bodily fluids and other materials in the environment. The protective sheathing, although transparent, can additionally encumber the caregiver's view of the surgical site 30.

Real-time video can be used to provide preferred visual access of the surgical site 30. Traditionally, video display may be provided on a monitor 32 as shown in FIG. 2 for viewing by caregiver 22. Video input for the display can be provided by one or more surgical cameras, for example, a da Vinci camera (robotic surgical camera) connected to one robotic appendage 20, which may be more easily positionable to have a desirable view than the human eye, given the encumbered environment near the surgical site 30.

However, the available arrangements of the monitor 32 can be constrained by the environment. This can require the caregiver 22 to change field of view, often requiring articulation of the caregiver's head and/or movement of the caregiver's body between viewing the surgical site 30 and viewing the monitor 32, at least within comfortable viewing positions for the caregiver 22. For example, the caregiver 22 may have to turn her head considerably to change between the different fields of view indicated by arrows 34 and 36 pertaining to monitor 32 and surgical site 30, respectively, as shown in FIG. 2.

Although the monitor 32 could potentially be moved to certain other locations about the surgical site 30 with consideration for the numerous instruments and/or equipment, the spatial requirements of the instruments and/or equipment can constrain the arrangement of the monitor 32. Caregiver 22 time and/or attention can be lost by time and/or effort in repositioning physical monitor 32 during the surgical procedure. Moreover, it can be desirable to maintain a large monitor, within sufficiently close range to provide the caregiver 22 with desired clarity and/or detail of the video display, which can further constrain the available arrangements of the monitor 32.

Figure 3:
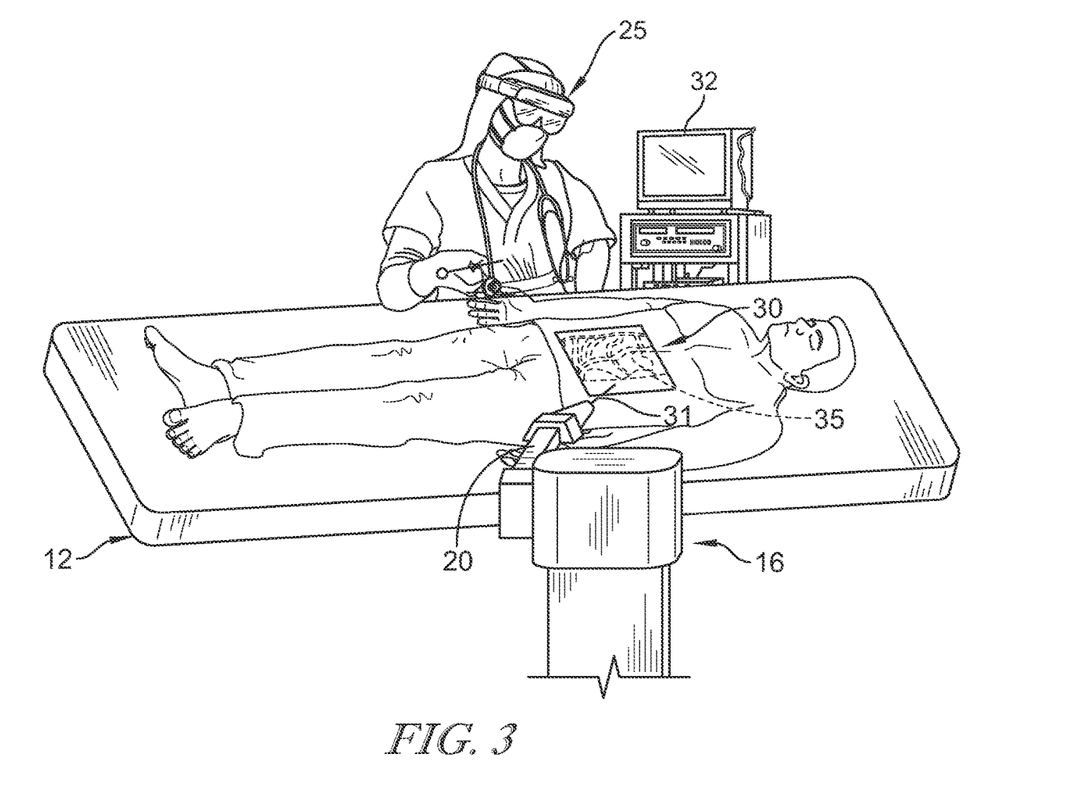
FIG. 3 is a perspective view of a patient surgical site indicating an augmented visual reality including imposition of patient internal organs into the augmented field of view of the caregiver.

Referring now to FIG. 3, augmented reality can be employed in patient procedures to assist with visualization of available information. For example, as depicted in FIG. 3, wearable goggles or glasses 25 for implementing augmented reality to superimpose, overlay, and/or otherwise display images of patient internals 35 in relative location (internal to the patient) can provide significant information within the visual field. The patient internals 35 are illustrative shown in broken line to indicate that they are within the patient but viewable as an augmented visual without retraction of the patient's skin or other body parts. As suggested by FIG. 3, the use of augmented reality systems can face challenges of visual obstruction of the relevant patient site 30, such as encumbrance by tools and/or instruments 33, including robotic appendages 20. Augmented reality systems can also face challenges in utilizing physical monitors 32 for display of patient images, such as the need for considerable movement and/or change in the caregivers 22 point of view in order to observe the monitor 32.

Figure 4:
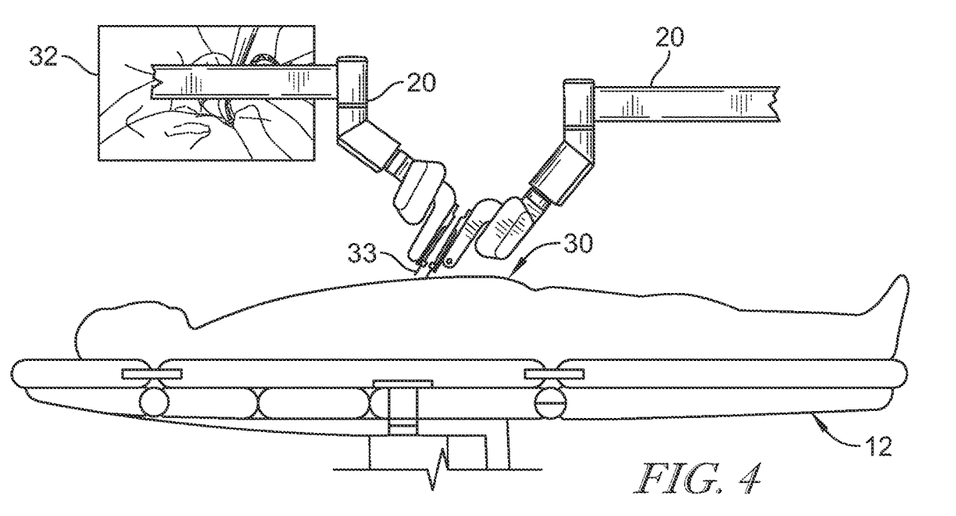
FIG. 4 is a side elevation view of a patient being addressed by a robotic surgical system showing that a monitor, providing preferred visual information of the surgical site for the caregiver to observe, is obstructed by robotic arms of the robotic surgical system.

As shown in FIG. 4, monitor 32 is arranged in proximity of the patient site 30. However, view of the monitor 32 is obstructed by the robotic appendages 20 addressing the patient. Yet, moving the monitor 32 in front of the robotic appendages 20 (out of the page) could likewise obstruct the physical access to the patient site 30 as the caregiver 22 (i.e., as illustratively viewed from the reader's perspective).

Figure 5:
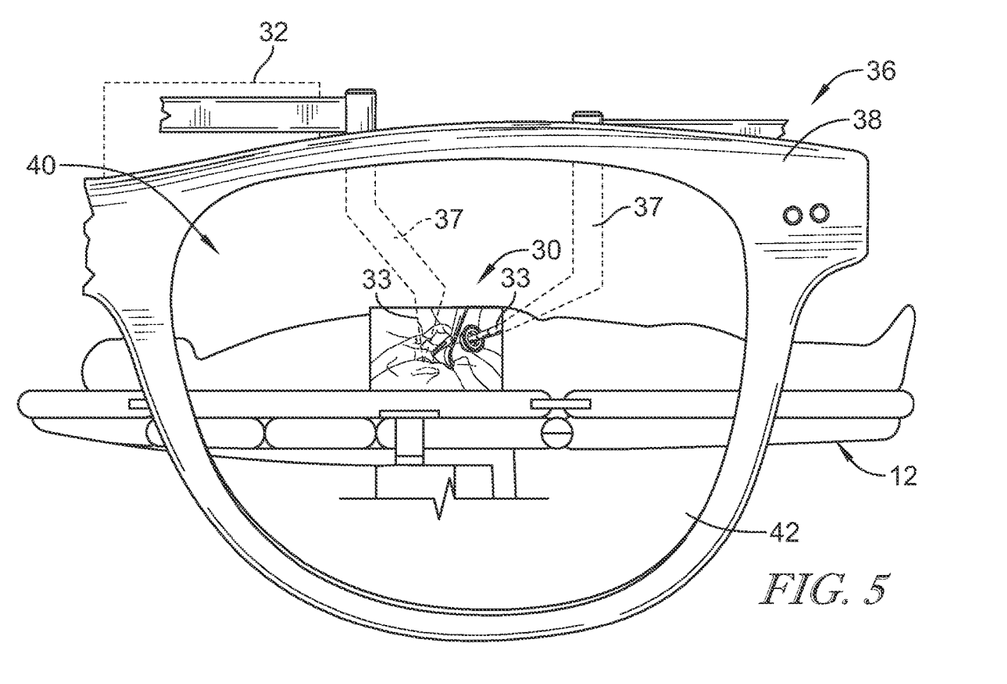
FIG. 5 is a side elevation view, similar to FIG. 4, showing an exemplary view of an augmented reality of a patient surgical site, from a caregiver's point of view, provided through an augmented visual field via lenses of the augmented reality system, showing that portions of the robotic arms have been removed from the visual field such that the surgical site and/or the position of surgical instruments can be more easily viewed.

As shown in FIG. 5, an augmented reality system 36 is shown for presenting visual access to the patient site 30 with artificial omission of certain obstructions. An exemplary framework 38 is shown indicating an augmented visual field 40 provided by wearable lenses 42 of the augmented reality system 36. The caregiver 22 wearing the lenses 42 to see through an optical lens, can observe the augmented environment provided by the augmented visual field 40 via the lenses 42. Although the augmented visual field 40 is illustratively embodied to include visual augmentation, the augmented visual field 40 can refer to the entire field of view via the lenses 42 which is available for augmented reality whether or not augmentation is performed at a given time or location within the augmented visual field 40 as defined by the framework 38 of the lenses 42. The framework 38 can include frameworks which omit complete annular frame structure, such as semi-rimless or rimless arrangements.

Notably, in FIG. 5, instruments 33 mounted on the robotic appendages 20 and monitor 32 which are within the field of view delimited by the framework 38 which would be expected to obstruct the present view are omitted from the augmented visual field 40, reducing impediment to the visual presentation of the patient site 30. This can be observed by comparison with the portions 37 of the robotic appendages 20 and portions of monitor 32 which are outside the field of view delimited by the framework 38. In the illustrative embodiment, the particular instruments 33, which are presently secured with each robotic appendage 20, remain visible in the augmented visual field 40. In some embodiments, some or all of selected robotic appendages 20, instruments 33, and/or other features may be included, excluded, and/or partially removed from the augmented visual field 40, and/or may be selectively adjusted between inclusion, exclusion and/or partial removal from the visual field 40 according to system settings. In the illustrative embodiment, as the user changes the range of the augmented visual field 40, for example, by moving her head, additional portions of the appendages 20 can be omitted from the augmented visual field 40 as discussed in additional detail below.

In the illustrative embodiment of FIG. 5, the patient site 30 is shown having augmented reality to show patient internals at the patient site 30, in addition to omitting the instrument obstructions. In some embodiments, the augmentation to show patient internals may be omitted and/or may include a variety of depths of internal visualization of the patient site 30, for example, subcutaneous, skeletal, vascular, other organ systems or tissue, and/or the like.

Figure 6:
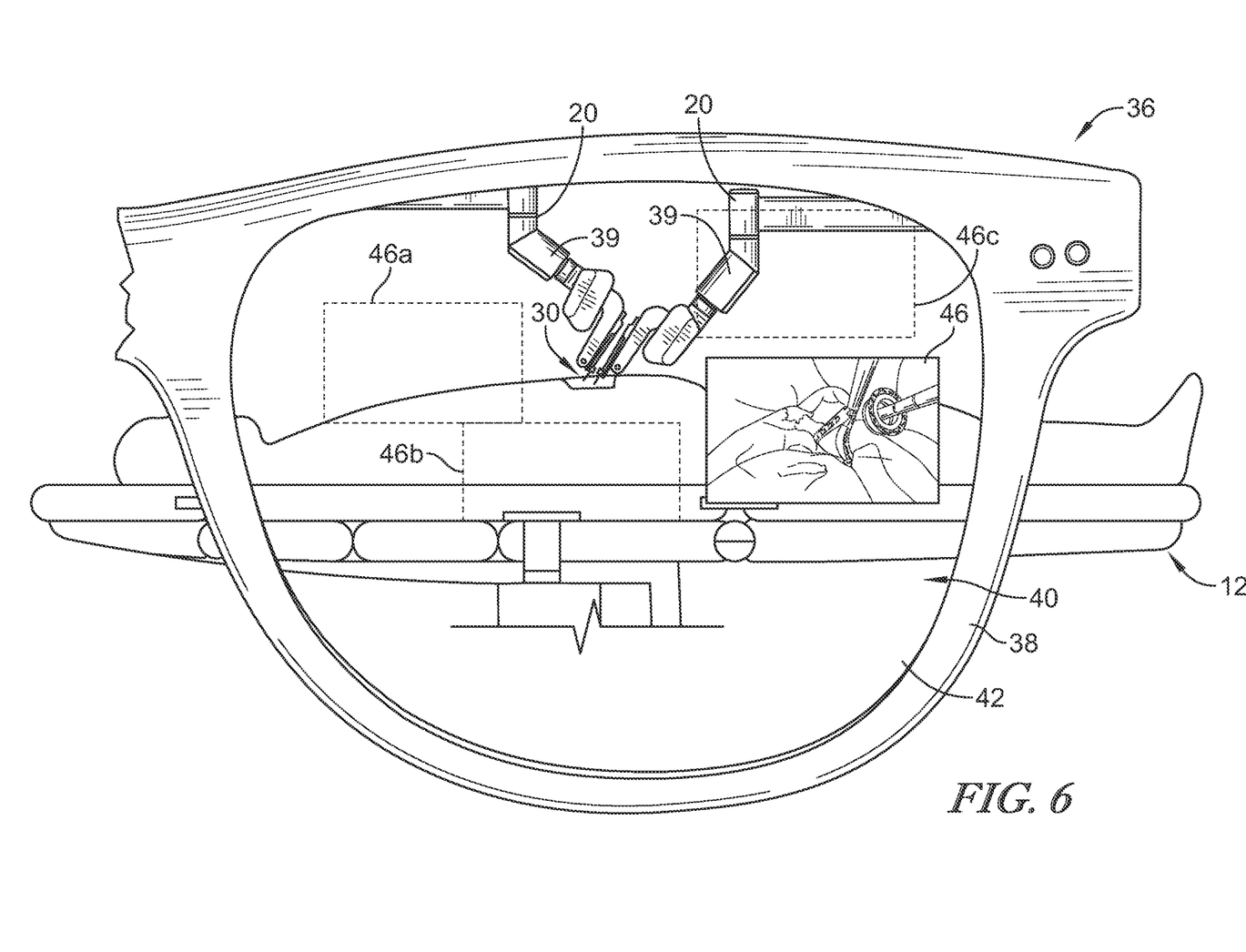
FIG. 6 is a side elevation view, similar to FIG. 5, showing that the augmented visual field includes a virtual monitor for viewing the surgical with additional visual augmentation, and showing that the virtual monitor can be moved to have a variety of locations relative to the surgical site to be unobstructed, for example, by robotic surgical arms or instruments.

Referring now to FIG. 6, the augmented visual field 40 includes a virtual monitor 46. The virtual monitor 46 is illustratively embodied as a visual augmented reality representation of a visual display within the augmented visual field 40. As discussed in additional detail below, the virtual monitor 46 is positionable within any variety of positions as relative to the patient site 30, such exemplary positions being indicated as positions 46a-46c. In the illustrative embodiment as shown in FIG. 6, the augmented visual field 40 has been configured not to omit portions 39 of the robotic appendages 20, although such portions 39 can be omitted based on the user input configuration of the augmented reality system 36.

Figures 7, 8:
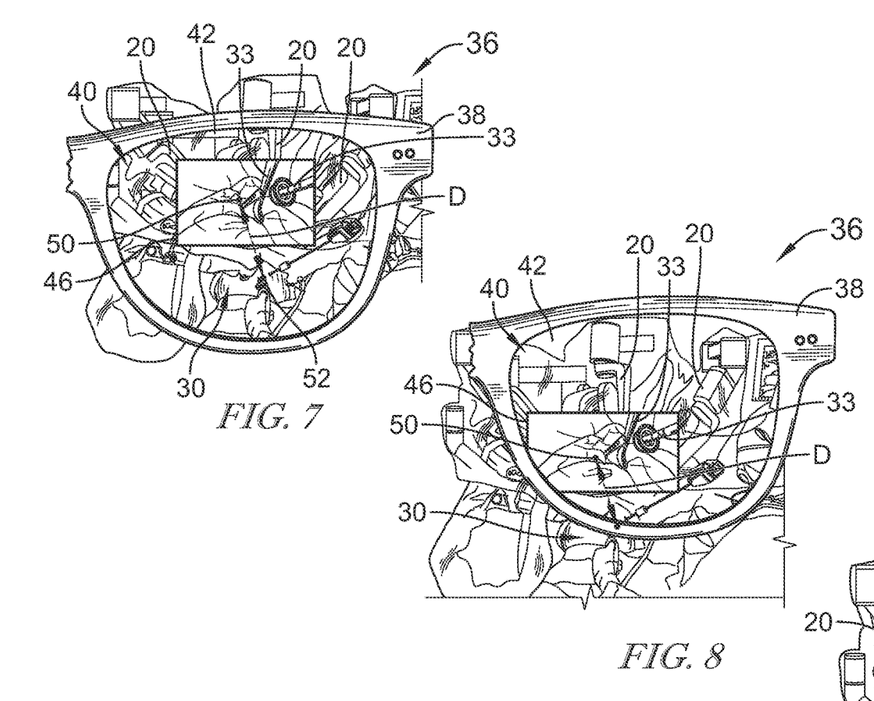
FIGS. 7-9 are perspective views of a surgical site showing that the virtual monitor is selectively positioned with an offset from the surgical site, and showing that the virtual monitor can be presented to remain fixed in place relative to motion of the lenses through which the caregiver is viewing the surgical site, for example, such that in FIGS. 8 and 9, as the caregiver moves her head, the virtual monitor appears to remain in place as a physical monitor.
Figure 9:
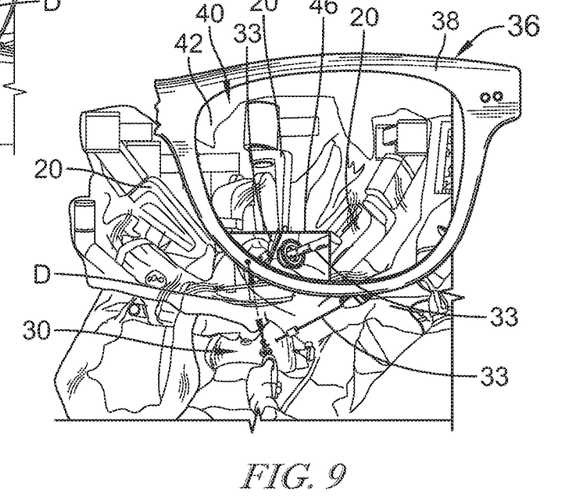

Referring now to FIGS. 7-9, operative movement of the caregiver 22 is illustrated. For example, in FIG. 7, the caregiver 22 wearing the lenses 42, of which only a portion of the framework 38 is shown, is presently viewing the patient site 30 and the caregiver's head is positioned in a relatively direct arrangement towards the patient site 30 such that the entire patient site 30 is within the augmented visual field 40. In FIG. 7, the virtual monitor 46 is illustratively positioned offset from the patient site 30. More specifically, the center 50 of the virtual monitor 46 is presently offset from the center 51 of the patient site 30 by a distance D above the patient site 30. Even without the virtual monitor 46 presenting a view of the patient site 30 which omits any obstruction that would ordinarily be observed from the camera's viewpoint, the caregiver 22 can view the virtual monitor 46 in a closely offset position to reduce movement and/or strain in accessing the virtual monitor 46.

Referring now to FIG. 8, the caregiver 22 has repositioned her head slightly upward to the right, for example, by standing and/or tilting her head upward and rightward relative to the patient site 30. Notably, the virtual monitor 46 has remained stationary relative to the patient site 30, despite movement of the lenses 42. Maintaining the virtual monitor 46 stationary from the perspective of the caregiver 22 can assist in creating a realistic feeling of the virtual monitor 46 as a physical display for the caregiver 22.

Referring now to FIG. 9, the caregiver 22 has repositioned her head even more upward to the right, for example, by standing and/or tilting her head upward and rightward relative to the patient site 30. The virtual monitor 46 has remained stationary relative to the patient site 30, despite further movement of the lenses 42. Notably, with the present position of the caregiver's head, a portion (lower left portion) of the virtual monitor 46 is now beyond the extent of the augmented visual field 40 and thus is not observable to the caregiver 22.

In moving between the positions exemplified by FIGS. 7-9, the caregiver 22 would likewise observe the virtual monitor 46 as stationary, and such stationary arrangement is applicable throughout any suitable range of motion of the caregiver 22 applying the lenses 42. Thus, a magnitude and direction of distance D between the center 51 of the patient site 30 and the center 50 of virtual monitor 46 remains fixed as lenses 42 are moved by the caregiver's head movement. Although in FIGS. 7-9, in the present configuration of the augmented reality system 36, the robotic appendages 20 are not excluded from the augmented visual field 40 beyond the virtual monitor 46, the augmented reality system 36 may be configured to selectively exclude from the augmented visual field 40 and/or display of the virtual monitor 46 some or all of the robotic appendages 20, instruments, and/or other potential visual obstructions.

Figure 10:
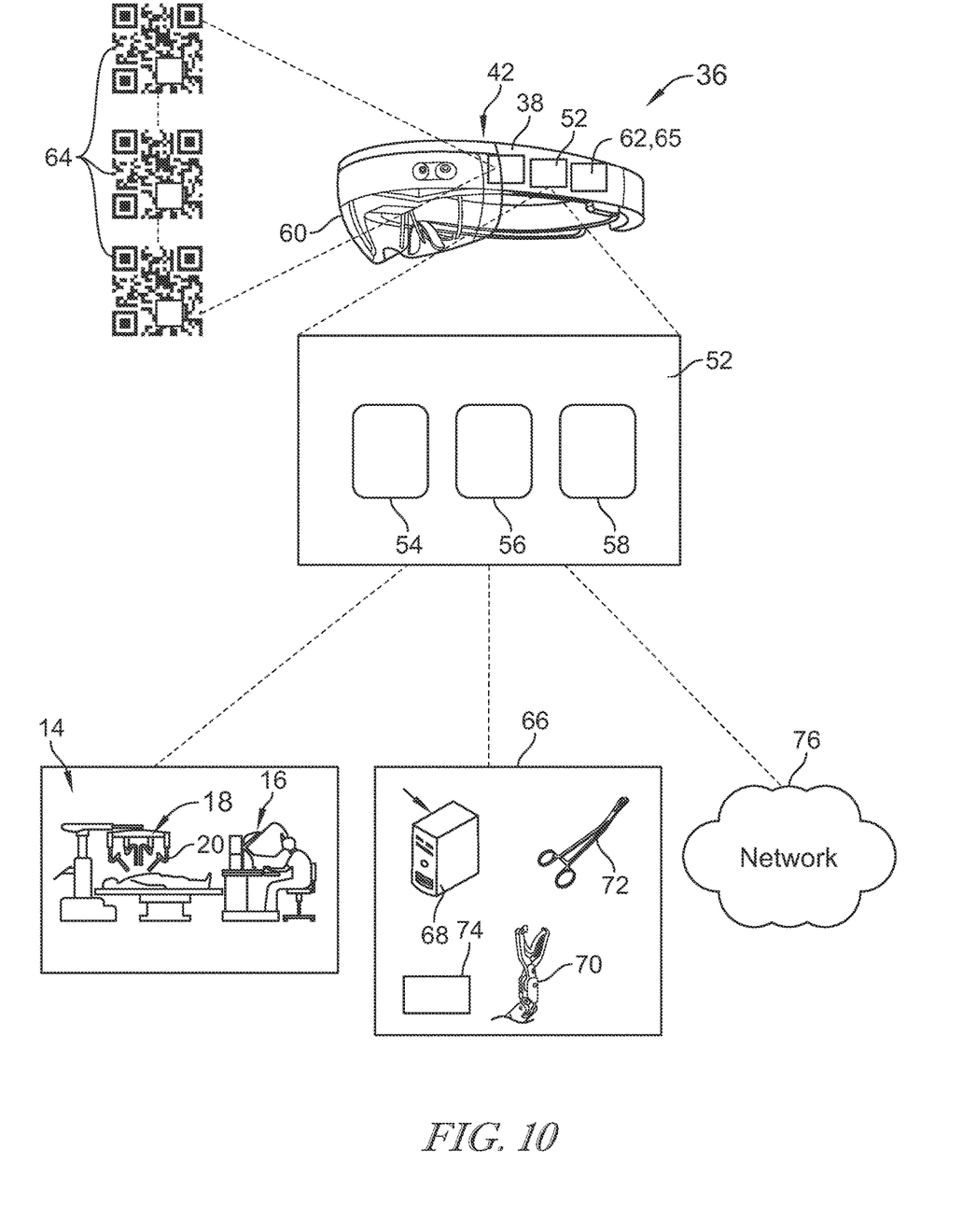
FIG. 10 is a diagrammatic view of the augmented reality surgical system showing that the lenses are arranged in communication with the augmented reality control system to receive instruction for presentation of the augmented reality for user viewing, and showing that the control system can receive indication of markers within the surgical environment to provide position orientation information to assist with visual augmentation, and showing that the augmented reality control system can communicate with the robotic surgery system, other tools of the surgical area, and/or networks.

Referring now to FIG. 10, the augmented reality system 36 is shown in diagrammatic form including an augmented reality control system 52 for conducting augmented reality system 36 operations. The augmented reality control system 52 illustratively includes a processor 54, memory 56, and communication circuitry 58. Processor 54 is configured to execute instructions stored in memory 56 to provide governing control and/or communications for augmented reality system 36 operations. Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM. DVD-ROM), RAM DRAM. SRAM. DRDRAM), ROM (e.g., PROM, EPROM, EEPROM, Flash EEPROM), volatile, and/or non-volatile memory; among others. Communication circuitry 58 includes components for facilitating processor operations, for example, suitable components may include transmitters, receivers, modulators, demodulator, filters, modems, analog to digital converters, operational amplifiers, and/or integrated circuits.

In the illustrative embodiment as shown in FIG. 10, the augmented reality control system 52 is arranged as a subcomponent of the lenses 42 in communication with a lens display 60 for providing the augmented visual field 40 which the caregiver 22 can view while wearing the lenses 42. However, in some embodiments, the augmented reality control system 52 may be arranged partly or wholly distinct from the lenses 42, in communication therewith, either wired or wirelessly, and the lenses 42 may include a local processor, memory, and/or communication components.

The lenses 42 illustratively include at least one sensor 62 to accommodate the relative positioning of the augmented reality information of the augmented visual field 40 presented by the lenses 42. The sensor 62 is arranged to capture the position of at least one field marker 64 arranged within the procedural environment to assist in determining relative positioning. In the illustrative embodiment, the sensor 62 includes a video camera for providing video and/or still imaging correlated to the position of the augmented visual field 40. Images from the sensor 62 can be analyzed by the augmented reality control system 52 to determine the specific location of the field markers 64. In some embodiments, the sensor 62 may include light scanning, wireless communications, and/or other manner of determining relative position, and may employ time of flight, triangulation, and/or other suitable techniques. The field markers 64 may be arranged in various positions within the surgical field, for example, on or about the patient, equipment, and/or room.

The lenses 42 illustratively include one or more sensors 65 for determining the relative position of the framework 38. The sensors 65 can include position sensors, tilt sensors, accelerometers, gyroscopic sensors, and/or any other suitable sensors for determining the relative position of the framework 38 such that the augmented visual field 40 can be appropriately configured in real time. The sensors 65 can include light sensors for determining visual aspects of the environment for desirable configuration of the augmented visual field 40. In some embodiments, the augmented reality system 26 may include and/or communicate with sensors, such as cameras, within the operating room (e.g., mounted of ceiling, walls, boom, surgical table, and/or robot arm) to determine the position of the framework 38 for generating appropriate augmented visual field 40.

In the illustrative embodiment, the field marker 64 is arranged on the patient support 12 as a reference point for the lenses 42 which can be calibrated with the patient's body position on the patient support 12. For example, a patient can be arranged on a surgical table as the patient support 12, and the augmented reality control system 52 may evaluate and record locations of the patient's body relative to the field markers 64 as part of a calibration of the augmented reality control system 52. The position of the patient body can then be known and/or checked according to the position of the one or more field markers 64. Field markers 64 can be arranged on instruments and/or on surfaces of the surgical environment, for example, the ceiling of the surgical environment to assist orientation of the augmented visual field 40.

Referring still to FIG. 10, the augmented reality control system 52 is arranged in communication with the robotic surgical system 14. The augmented reality control system 52 can communicate with the robotic surgical system 14 to provide information regarding the robotic personage 18 and/or other aspects of the procedure. For example, the positions of the robotic appendages 20 and/or the image feed input from the camera mounted to the robotic appendages 18 can be communicated with the augmented reality control system 52 to assist in accuracy and/or precision in the augmented visual field 40 presented by the lenses 42.

The augmented reality control system 52 can be arranged in communication with various local devices and/or systems 66. Such local devices and/or systems 66 can include local surgical servers 68 for administration of the procedure itself, instruments such as robotic instruments 70 and/or manual instruments 72, local audio/visual devices such as cameras 74, and/or other local equipment. Communication with local equipment can provide nearly instantaneous information, can reduce dependence on resources outside of the surgical environment, and/or can isolate critical information exchange which itself can increase reliability and/or security of information. In some embodiments, some or all of the augmented reality control system 52 may be provided by the local surgical servers 68.

The augmented reality control system 52 can be arranged in communication with a communication network 76. The communication network 76 is illustratively embodied as a hospital network providing access to any variety of hospital records and/or communications. In some embodiments, the communication network 76 may provide communication and/or access to other external networks and/or systems, such as general internet, remote database systems and/or networks. The communication network 76 can be implemented to allow the augmented reality control system 52 to obtain information from other resources and/or to allow communication of information to other resources, for example, for record keeping, administration, and/or surgical purposes such as to update organ transplant personnel of current status information.

Figure 11:
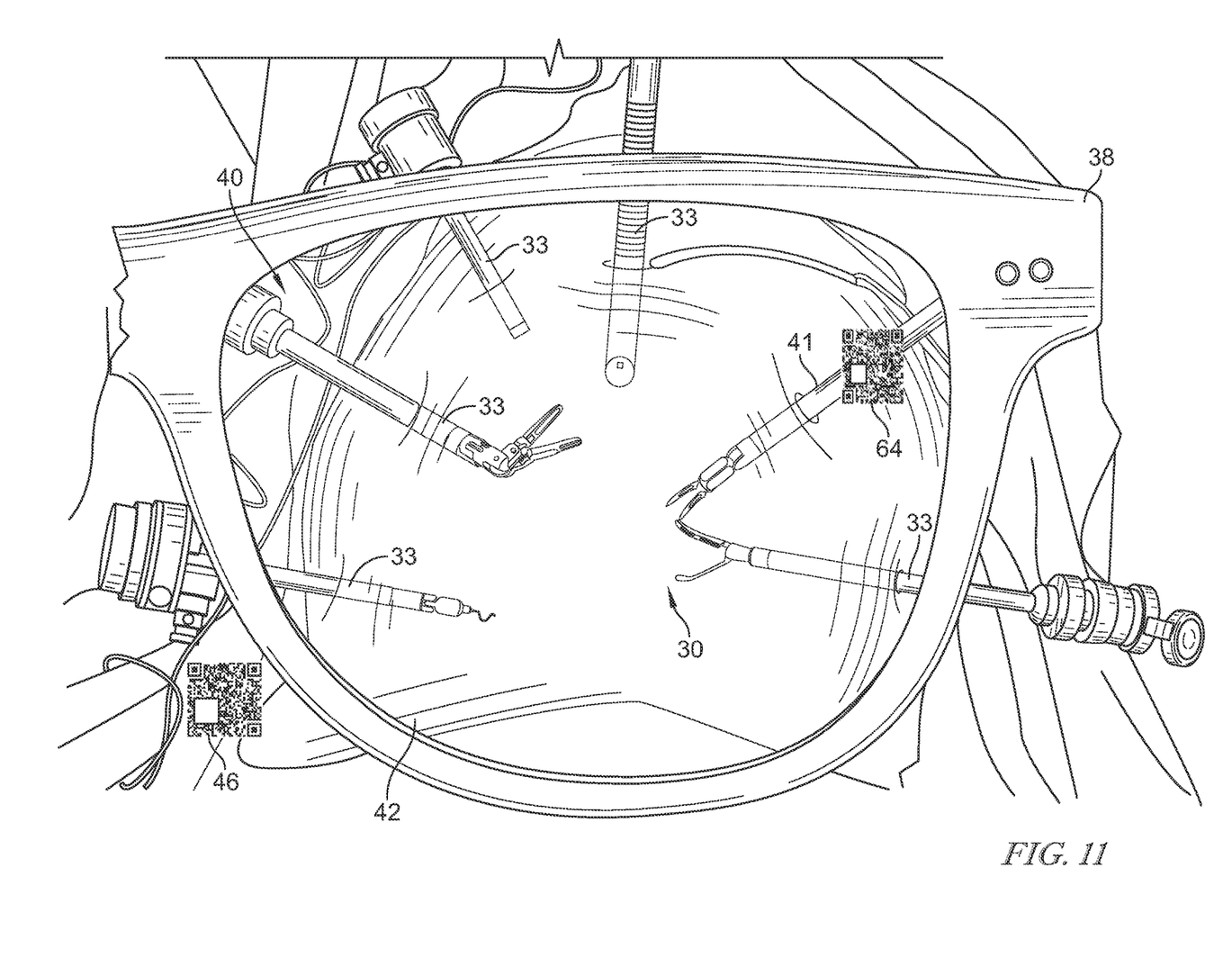
FIG. 11 a perspective view of the patient surgical site showing an exemplary augmented visual field in which extension of various surgical instruments into the patient's body (laparoscopically) can be shown, and indicating that at least one of the surgical tools includes a marker for indicating its relative position for use in providing the augmented visual field.

Referring now to FIG. 11, an exemplary augmented visual field 40 is shown at the patient site 30. In the augmented visual field 40, internal projections of various instruments 41 of the robotic appendages 20 into the patient are presented. A field marker 64 is shown secured to one of the instruments 41 for allowing determination and/or checking of the relative position of the augmented visual field 40. The lenses 42 can detect the position of the field marker 64 by sensor 62 and/or by analysis of images of the augmented visual field 40. In some embodiments, the position of the field marker 64 may be communicated with the robotic surgery system 16 for consideration in conducting the surgical procedure.

Figure 12:
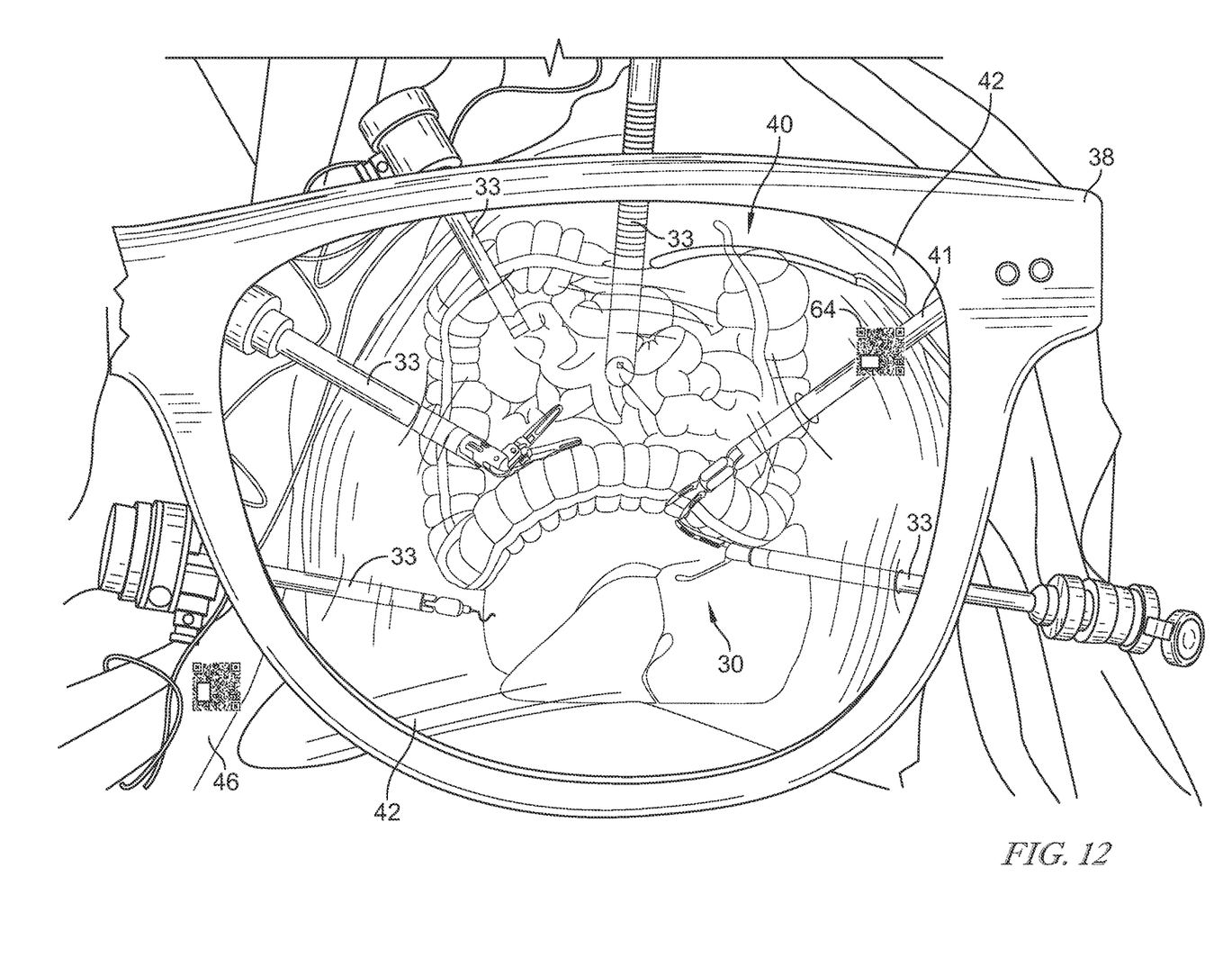
FIG. 12 is a perspective view of the patient surgical site, similar to FIG. 11, showing that patient internals including organs are depicted in the augmented visual field.

As shown in FIG. 12, in addition to the internal projections of various instruments 33 of the robotic appendages 20, the augmented visual field 40 is shown including representations of the patient's internal organs near the surgical site 30. Presenting to the caregiver 22 the augmented visual field 40 with depiction of arrangements internal to the patient can provide the caregiver 22 more confidence of staying up-to-speed with the on-goings of the procedure performed by the surgeon, can decrease the risk of errors, and/or increase safety of the procedure generally. For example, the caregiver 22 can confirm that the location and/or orientation of an internal surgical instrument displayed in the augmented visual field 40 corresponds with the known and/or announced current stage of the procedure. If non-correspondence is observed, the caregiver 22 can communicate directly with other surgical team members to confirm her understanding of the stage of the procedure providing opportunities to correct oversights in real time.

Figure 13:
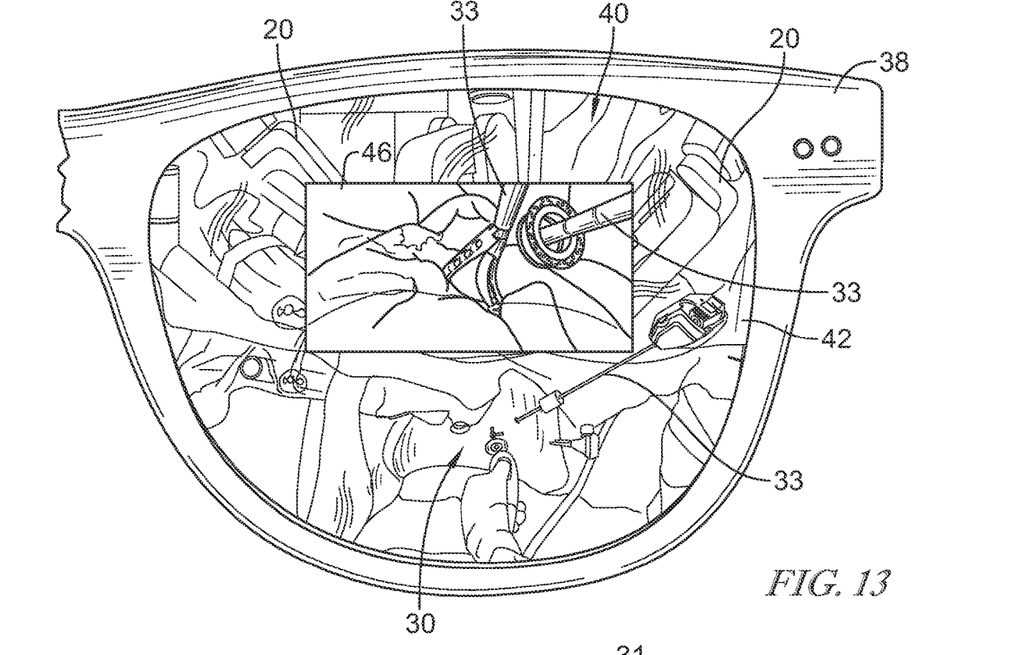
FIG. 13 is a perspective view of a patient surgical site having augmented visual field provided by the augmented virtual reality system of FIGS. 3-12 to include a virtual monitor showing that the monitor has a set size and position relative to the patient surgical site.
Figure 14:
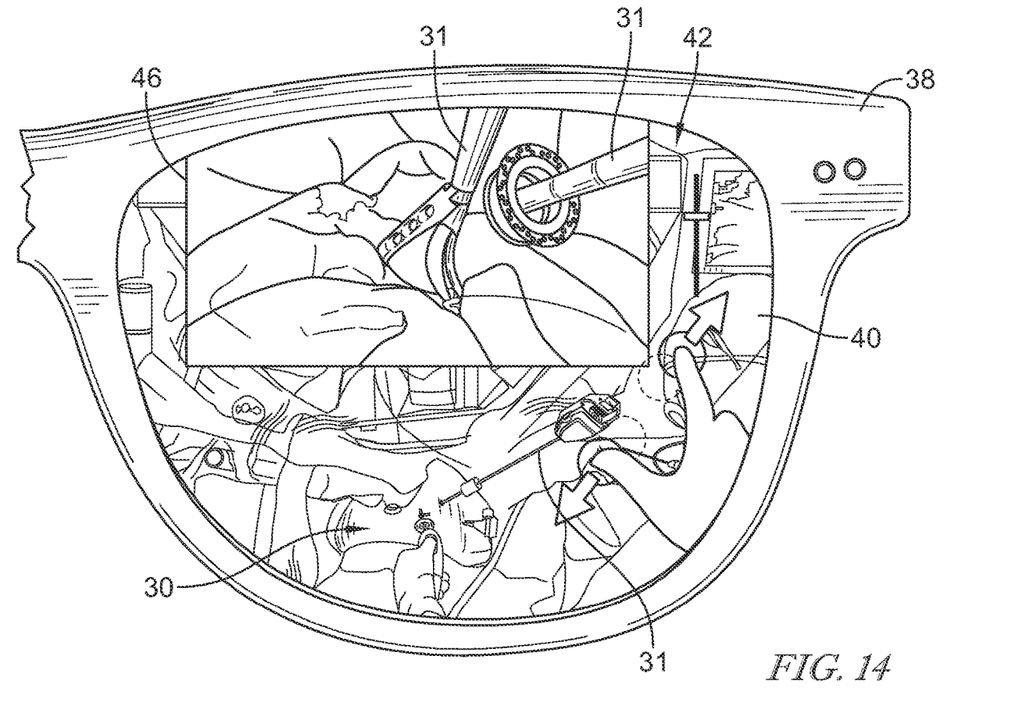
FIG. 14 is a perspective view of the patient surgical site, similar to FIG. 13, showing that the user has resized the virtual monitor using a hand gesture.

Referring now to FIGS. 13 and 14, the augmented visual field 40 is shown including the virtual monitor 46. The initial location and/or size of the virtual monitor 46 is illustratively set as a system default, and the caregiver 22 can call up or initiate the virtual monitor 46, for example, by user input by button or hand gesture such as a swipe of sufficient length, recognized as input by one or more of the sensors 62, 65.

In FIG. 13, the virtual monitor 46 is shown having been called up by the user and having a first location and size. In FIG. 14, the caregiver 22 has used a gesture, indicated by spreading of two fingers, to enlarge the virtual monitor 46 within the augmented visual field 40. The caregiver 22 can thus adjust the settings of the virtual monitor 46 using gestures which can be detected by the one or more of the sensors 62, 65.

The caregiver 22 can reposition the virtual monitor 46 by unique command call, such as forming an L-shape between the thumb and index finger and then dragging the virtual monitor 46 to the desired location. Although adjustments have been described in the context of particular gestures, the augmented reality surgical system may be configured to recognize any suitable manner of gesture for adjustment of the virtual monitor 46, including but not limited to gestures for call up of virtual controls such as sliders, dials, and the like. Similarly, graphical adjustment, such as adjustment of color, resolution, detail, brightness, contrast, gamma, balance and/or any other suitable aspects of display of the virtual monitor 46 can be adjusted by recognized gesture. The user may define a new default position and/or size of the virtual monitor 46 by additional unique gesture, such as thumbs up held for minimum threshold duration.

Caregiver gestures can operate any number of features of the lenses 42, for example, a unique gesture can be used to perform a "screen capture" or digital photograph of the augmented visual field 40 and/or virtual monitor 46 at any moment during the procedure. For example, the user may mimic pressing a conventional camera capture button (e.g., depressing a top mounted capture button) to initiate screen capture. In some embodiments, any suitable caregiver input may be applied to perform screen capture, for example, a physical button on the lenses 42. The screen capture may be conducted by the augmented reality control system 52 and stored by one or more of the memory 56, on local servers, and/or on server of network 76, for example, the screen capture can be stored in the patient's medical record via the network 76.

Achieving proper visualization of the surgical site during robotic surgery can be essential for the surgeon and supporting surgical staff, but this is not always easily achieved. Immersion efforts observing robotic surgeries have revealed opportunities associated with visualization. Even large operating rooms can experience crowding around the patient by equipment, monitors, instruments, and/or staff. For example, it is common to have six or more monitors around the patient, and booms and/or carts that support these monitors can take up even more room. These monitors can create issues with workflow, for example, as staff bump into monitors or ask one another to adjust their view.

Although the staff are often crowded around the patient, their necks are typically craned to look at monitors placed in the periphery. This causes physical discomfort and/or can divert attention away from the patient. These sorts of encumbrances can also create cognitive burden as the DaVinci camera is aimed and oriented in alignment with the surgeon's view, not the viewpoint and position of the assisting staff. This cognitive burden slows response times and causes errors. Additionally, surgeons can benefit from 3D vision using the DaVinci whereas the supporting staff can be relegated to 2D vision. This can create challenges when handing off instruments, devices, and/or tissue inside the patient which is common.

The present disclosure includes augmented reality (AR) glasses worn by the surgical team. The glasses may detect location reference markers on the OR table, DaVinci robotic boom, and/or operating room itself to facilitate operations. The glasses may be arranged in communication with the DaVinci robot which has information/knowledge of the location of its instruments in 3D space. The glasses may use the reference markers to determine the location of the user in 3D space relative to the patient. An overlay can be mapped onto or above the patient to display information.

Devices, systems, and methods within the present disclosure may include displaying a virtual monitor above the patient that looks similar to a standard LCD monitor but using 3D from the stereoscopic DaVinci camera, rendering the DaVinci instruments in the patient overlaid on the patient, and/or rendering the DaVinci instruments and patient anatomy overlaid on the patient. The user can be enabled to move and/or adjust these AR renderings using a physical interface and/or gestural controls (for example, pinching and moving the hand to adjust the location of the virtual screen relative to the patient).

Within the present disclosure, descriptions and/or illustrations pertaining to a single set of wearable lenses 42 have been discussed, however, in some embodiments, different caregivers may each have a pair of lenses 42 of the augmented reality system 36. Different lenses 42 can be configured for different manner of augmented visual field 40. For example, one caregiver's lenses 42 can be configured to have a first position, size, detail of augmentation, visual image (e.g., contrast, illumination, etc.), and/or the like, while simultaneously a second caregiver's lenses can be configured to have a second position, size, detail of augmentation, visual image (e.g., contrast, illumination, etc., such as to emphasize a particular tissue and/or instrument), and/or the like, any one or more of which being different from the first. In application, caregivers can have personalized augmented visual fields 40 which suit their preference and/or their task in assisting the surgical procedure. Moreover, the augmented visual field 40 for each lens 42, and any virtual monitor 46 therein, can be particularly oriented according to the wearer. Accordingly, wearer-personalized augmented visual fields can be presented.

Although certain illustrative embodiments have been described in detail above, variations and modifications exist within the scope and spirit of this disclosure as described and as defined in the following claims.

I claim:

1. A surgical augmented reality system, comprising:
an optical lens through which a user can directly observe surgical procedures, the optical lens defining a field of view and configured for presenting visual information augmenting observation of the user;
an augmented reality control system in communication with the optical lens to provide presentation of visual information augmenting observation by the user, the augmented reality control system comprising at least one processor, at least one memory storage for storing instructions for execution by the at least one processor, and communication circuitry for communicating signals according to the processor, the augmented reality control system configured to receive indication of at least one reference datum and to communicate with the optical lens to provide an augmented reality presentation of a surgical area of the patient artificially omitting one or more obstructions from the user's view point of the surgical area within the field of view,
wherein the augmented reality presentation includes a virtual monitor for viewing the surgical area with augmentation, wherein the virtual monitor is visually arranged within the optical lens offset from the surgical area of the patient to appear as an offset view screen, wherein the augmented reality control system is configured to display the surgical area within the field of view including a viewpoint configuration having visual augmentation of the surgical area and to display the virtual monitor including a monitoring configuration having visual augmentation of the surgical area, different from the viewpoint configuration.

2. The surgical augmented reality system of claim 1, wherein each of the viewpoint configuration and the monitoring configuration are selectively configurable by the augmented reality system to omit different aspects from the user's view point of the surgical area.

3. The surgical augmented reality system of claim 1, wherein the augmented reality presentation includes display of the augmented reality presentation visually arranged in the optical lens for observation by the user to appear stationary with reference to the surgical area under relative movement of the optical lens.

4. The surgical augmented reality system of claim 1, wherein the optical lens is configured as a wearable lens.

5. The surgical augmented reality system of claim 4, wherein the optical lens is formed as a set of optical glasses comprising at least one sensor for capturing indication of a position of the at least one reference datum.

6. The surgical augmented reality system of claim 5, wherein the at least one reference datum includes one or more reference datum arranged on a ceiling of an operating room of the patient.

7. The surgical augmented reality system of claim 5, wherein the at least one reference datum includes one or more reference datum arranged on a surgical patient support table.

8. The surgical augmented reality system of claim 1, wherein the augmented reality control system is arranged in communication with a surgeon interface for control of a robotic surgery device.

9. The surgical augmented reality system of claim 1, wherein the augmented reality control system is arranged in communication with a remote network.

10. The surgical augmented reality system of claim 9, wherein the remote network is a hospital network.

11. The surgical augmented reality system of claim 1, wherein the augmented reality control system is arranged in communication with one or more local surgical devices.

12. The surgical augmented reality system of claim 11, wherein the one or more local surgical devices include at least one of a local server and local surgical instruments.

13. The surgical augmented reality system of claim 1, wherein the augmented reality control system is arranged at least partly on a wearable device comprising the optical lens.

14. The surgical augmented reality system of claim 1, wherein the augmented reality control system is arranged at least partly on a surgical server.

15. The surgical augmented reality system of claim 1, wherein the augmented reality presentation is arranged by the optical lens to overlay the surgical area of the patient to create impression of direct observation.

* * * * *